United States Patent
Desai et al.

(10) Patent No.: US 9,682,066 B2
(45) Date of Patent: Jun. 20, 2017

(54) METHODS OF TREATING PRIMARY BRAIN TUMORS BY ADMINISTERING LETROZOLE

(71) Applicant: University of Cincinnati, Cincinnati, OH (US)

(72) Inventors: Pankaj Desai, Cincinnati, OH (US); Nimita Dave, Cincinnati, OH (US)

(73) Assignee: University of Cincinnati, Cincinnati, OH (US)

( * ) Notice: Subject to any disclaimer, the term of this patent is extended or adjusted under 35 U.S.C. 154(b) by 235 days.

(21) Appl. No.: 14/096,536

(22) Filed: Dec. 4, 2013

(65) Prior Publication Data

US 2014/0154244 A1 Jun. 5, 2014

Related U.S. Application Data

(60) Provisional application No. 61/732,976, filed on Dec. 4, 2012.

(51) Int. Cl.
*A61K 31/4196* (2006.01)
*A61K 45/06* (2006.01)

(52) U.S. Cl.
CPC .......... *A61K 31/4196* (2013.01); *A61K 45/06* (2013.01)

(58) Field of Classification Search
CPC ............................ A61K 31/4196; A61K 45/06
See application file for complete search history.

(56) References Cited

U.S. PATENT DOCUMENTS

| 2003/0139430 | A1* | 7/2003 | Resta | A61K 31/4196 514/265.1 |
| 2004/0176339 | A1* | 9/2004 | Sherman | A61K 31/4188 514/171 |
| 2010/0035257 | A1* | 2/2010 | Ellisen | G01N 33/57415 435/6.14 |

OTHER PUBLICATIONS

Stevens, Cleveland Clinic Center for Continuing Education Published Aug. 2010 (http://www.clevelandclinicmeded.com/medicalpubs/diseasemanagement/hematology-oncology/brain-tumors/Default.htm#s0055).*
Kirson et al. PNAS, Jun. 2007, vol. 104, No. 24, pp. 10152-10157.*
Minniti et al, Chemotherapy for glioblastoma: current treatment and future perspectives for cytotoxic and targeted agents. Anticancer Res 29, 5171-5184 (2009).
Pollack et al, Effect of tamoxifen on DNA synthesis and proliferation of human malignant glioma lines in vitro. Cancer Res 50, 7134-7138 (1990).
Silvera et al, Hormonal and reproductive factors and risk of glioma: a prospective cohort study. Int J Cancer 118, 1321-1324 (2006).
Dave et al, Brain/Brain Tumor Pharmacokinetics and Pharmacodynamics of Letrozole, University of Cincinnati presentation poster (2012).
Altinoz et al, The effects of tibolone on the human primary glioblastoma multiforme cell culture and the rat C6 glioma model. Neurol Res 31, 923-927 (2009).
Apparaju et al, Pharmacokinetics of gemcitabine in tumor and non-tumor extracellular fluid of brain: an in vivo assessment in rats employing intracerebral microdialysis. Cancer Chemother Pharmacol 61, 223-229 (2008).
Behl et al, Neuroprotective activities of estrogen: an update. J Neurocytol 29, 351-358 (2000).
Berny et al, Analysis of expression of estrogen (ER) and progesterone receptors (PR) in brain glial tumors and its correlation with expression of p53 protein and proliferating cell nuclear antigen (PCNA), Neurol Neurochir Pol 38, 367-371 (2004) (English Abstract Only—Polish language article not available through any channels.).
Brueggemeier et al, Aromatase inhibitors in the treatment of breast cancer. Endocr Rev 26, 331-345 (2005).
Buzdar et al, An overview of the pharmacology and pharmacokinetics of the newer generation aromatase inhibitors anastrozole, letrozole, and exemestane. Cancer 95, 2006-2016 (2002).
Carroll et al, Steroid hormone receptors in astrocytic neoplasms. Neurosurgery 37, 496-503; discussion 503-494 (1995).
Chamaon et al, Micromolar concentrations of 2-methoxyestradiol kill glioma cells by an apoptotic mechanism, without destroying their microtubule cytoskeleton. J Neurooncol 72, 11-16 (2005).
Chow et al, Cooperativity within and among Pten, p53, and Rb pathways induces high-grade astrocytoma in adult brain. Cancer Cell 19, 305-316 (2011).
Cos et al, Melatonin modulates aromatase activity in MCF-7 human breast cancer cells. J Pineal Res 38, 136-142 (2005).
Dhandapani et al, Protective effects of estrogen and selective estrogen receptor modulators in the brain. Biol Reprod 67, 1379-1385 (2002).
Diaz-Crus et al, Cyclooxygenase inhibitors suppress aromatase expression and activity in breast cancer cells. J Clin Endocrinol Metab 90, 2563-2570 (2005).
Eichler et al, The biology of brain metastases—translation to new therapies. Nat Rev Clin Oncol 8, 344-356 (2011).
Fujimoto et al, Estrogen receptors in brain tumors. Clin Neuropharmacol 7, 357-362 (1984).
Garcia-Segura, Aromatase in the brain: not just for reproduction anymore. J Neuroendocrinol 20, 705-712 (2008).
Garcia-Segura et al, Neuroprotection by estradiol. Prog Neurobiol 63, 29-60 (2001).
Gonzalez-Arenas et al, Estradiol increases cell growth in human astrocytoma cell lines through ERalpha activation and its interaction with SRC-1 and SRC-3 coactivators. Biochim Biophys Acta 1823, 379-386 (2007).
Goytal et al, Excellent response to letrozole in brain metastases from breast cancer. Acta Neurochir (Wien) 150, 613-614; discussion 614-615 (2008).

(Continued)

*Primary Examiner* — Kara R McMillian
(74) *Attorney, Agent, or Firm* — Dinsmore & Shohl LLP

(57) ABSTRACT

The present disclosure relates to the field of cancer treatment, and more specifically to the field of treatment of primary malignant brain tumors. Provided herein are methods of treating primary brain tumors, including gliomas, by administering to a patient in need thereof a therapeutically effective amount of the aromatase inhibitor letrozole.

18 Claims, 12 Drawing Sheets

(56) References Cited

OTHER PUBLICATIONS

Gril et al, Pazopanib reveals a role for tumor cell B-Raf in the prevention of HER2+ breast cancer brain metastasis. Clin Cancer Res 17, 142-153 (2011).

Haga et al, Involvement of the multidrug resistance protein 3 in drug sensitivity and its expression in human glioma. Jpn J Cancer Res 92, 211-219 (2001).

Horowitz et al, Regional [14C]misonidazole distribution in experimental RT-9 brain tumors. Cancer Res 43, 3800-3807 (1983).

Kabat et al, Do steroid hormones play a role in the etiology of glioma? Cancer Epidemiol Biomarkers Prev 19, 2421-2427 (2010).

Kabat et al, Reproductive factors and exogenous hormone use and risk of adult glioma in women in the NIH-AARP Diet and Health Study. Int J Cancer 128, 944-950 (2011).

Keating, Letrozole: a review of its use in the treatment of postmenopausal women with hormone-responsive early breast cancer. Drugs 69, 1681-1705 (2009).

Kuerer et al, Biologic basis and evolving role of aromatase inhibitors in the management of invasive carcinoma of the breast. J Surg Oncol 77, 139-147 (2001).

Lephart, A review of brain aromatase cytochrome P450. Brain Res Brain Res Rev 22, 1-26 (1996).

Lis et al, 2-Methoxyestradiol inhibits proliferation of normal and neoplastic glial cells, and induces cell death, in vitro. Cancer Lett 213, 57-65 (2004).

Liu et al, Gender difference in letrozole pharmacokinetics in rats. Acta Pharmacol Sin 21, 680-684 (2000).

Lonning, Clinical pharmacokinetics of aromatase inhibitors and inactivators. Clin Pharmacokinet 42, 619-631 (2003a).

Lonning et al, Pharmacokinetics of third-generation aromatase inhibitors. Semin Oncol 30, 23-32 (2003a).

Lonning, Comparison between aromatase inhibitors and sequential use. J Steroid Biochem Mol Biol 86, 275-282 (2003b).

Lonning et al, Development of aromatase inhibitors and their pharmacologic profile. Am J Clin Oncol 26, S3-8 (2003b).

Madhup et al, Letrozole for brain and scalp metastases from breast cancer—a case report. Breast 15, 440-442 (2006).

Myhre et al, Estrogen activates rapid signaling in the brain: role of estrogen receptor alpha and estrogen receptor beta in neurons and glia. Neuroscience 138, 851-858 (2006).

Naftolin, Brain aromatization of androgens. J Reprod Med 39, 257-261 (1994).

O'Shaughnessy, A decade of letrozole: FACE. Breast Cancer Res Treat 105 Suppl 1, 67-74 (2007).

Pfister et al, Effect of age and single versus multiple dose pharmacokinetics of letrozole (Femara) in breast cancer patients. Biopharm Drug Dispos 22, 191-197 (2001).

Pinski et al, Inhibition of growth of the human malignant glioma cell line (U87MG) by the steroid hormone antagonist RU486. J Clin Endocrinol Metab 77, 1388-1392 (1993).

Salvati et al, Prolonged stabilization of multiple and single brain metastases from breast cancer with tamoxifen. Report of three cases. Tumori 79, 359-362 (1993).

Santen et al, History of aromatase: saga of an important biological mediator and therapeutic target. Endocr Rev 30, 343-375 (2009).

Stewart et al, Response of brain metastases from breast cancer to megestrol acetate: a case report. J Neurooncol 24, 299-301 (1995).

Sun, Estrogen receptors in patients with brain tumors, Zhonghua Wai Ke Za Zhi 27, 299-300, 318 (1989).

Thaker et al, Molecularly targeted therapies for malignant glioma: rationale for combinatorial strategies. Expert Rev Neurother 9, 1815-1836 (2009).

Wempe et al, Pharmacokinetics of letrozole in male and female rats: influence of complexation with hydroxybutenylbeta cyclodextrin. J Pharm Pharmacol 59, 795-802 (2007).

Yague et al, Aromatase, the enzyme responsible for estrogen biosynthesis, is expressed by human and rat glioblastomas, Neuroscience Letters 368, 279-284 (2004).

Argyriou et al, Molecularly targeted therapies for malignant gliomas. Mol Med 15, 115-122 (2009).

Geisler et al, Aromatase inhibition: translation into a successful therapeutic approach. Clin Cancer Res 11, 2809-2821 (2005).

Gonzalez et al, Inhibitory effects of pharmacological doses of melatonin on aromatase activity and expression in rat glioma cells. Br J Cancer 97, 755-760 (2007).

Huang et al, Reproductive factors and risk of glioma in women. Cancer Epidemiol Biomarkers Prev 13, 1583-1588 (2004).

Kirches et al, 2-methoxyestradiol as a potential cytostatic drug in gliomas? Anticancer Agents Med Chem 9, 55-65 (2009).

\* cited by examiner

MTT assay

Aromatase activity EIA assay

A

B

C

D

A

B

C

D

METHODS OF TREATING PRIMARY BRAIN TUMORS BY ADMINISTERING LETROZOLE

RELATED APPLICATION

This application claims the benefit of U.S. Provisional Application No. 61/732,976 filed Dec. 4, 2012, which application is hereby incorporated by reference in its entirety.

FIELD OF THE INVENTION

The presently disclosed subject matter relates to the field of cancer treatment. Specifically, the present invention relates to methods of administering letrozole for the treatment of primary brain tumors.

BACKGROUND OF THE INVENTION

According to the Central Brain Tumor Registry of the United States (CBTRUS), as of March 2012, brain and central nervous system (CNS) tumors are the second leading cause of cancer-related deaths in children under age 20 and in males ages 20-39. Brain and CNS tumors represent the fifth leading cause of cancer-related deaths in females ages 20-39. According to 2010 statistics, more than 688,000 people were living with primary CNS tumors in the United States (Porter et al., *Prevalence estimates for primary brain tumors in the United States by age, gender, behavior, and histology, Neuro. Oncol.* 12:520-27 (2010)). Of those tumors, 138,000 were malignant tumors and 550,000 were nonmalignant tumors. CBTRUS estimated 69,720 new cases of primary brain tumors in 2013.

Treatment options for brain tumors include surgery, radiation therapy, and chemotherapy. The recommended therapy depends on several factors, such as size and type of tumor, whether the tumor is affecting any vital parts of the brain, and whether the tumor has metastasized to other parts of the CNS or the body.

One of the challenges to treating primary brain tumors with chemotherapeutic agents is the existence of unique physical features in the brain which prevent most therapeutic agents from accessing tumor tissue. First, the blood-brain barrier (BBB) restricts the passage of most endogenous and exogenous substrates from traversing the brain parenchyma. Brain endothelium cells differ from those in other organs. In other organs, intracellular clefts are found in the capillary beds and fenestrae are formed by the endothelial cells, which aid in diffusion of substrates into and across the endothelial cells. Brain endothelial cells have continuous tight junctions, an absence of fenestrations, and very low pinocytic activity. A basal membrane and extracellular matrix surround brain endothelial cells. Permeability is mainly controlled by astrocytic and pericytic foot processes covering most of the endothelial cell surface. Permeability is modulated by chemical factors and signals released by astroglia. Further, unique protein composition (including high expression of occluding proteins) creates high electrical resistance in brain capillaries, which forms a barrier against polar and ionic substances. Collectively, these features form a BBB that protects the brain, but which also prevents most therapeutic agents from entering the brain.

In the case of primary brain tumors, the blood-tumor barrier (BTB) provides a further challenge to delivering therapeutic agents to malignant tissue. In primary tumors such as gliomas, the BTB may be variably disrupted in the tumor and surrounding tissue. Portions of tumors with a mainly intact BTB may be shielded from chemotherapy, greatly complicating the ability to therapeutically treat such tumors.

Despite advances in treatment modalities for primary brain tumors, the overall prognosis remains poor. Given the increasing prevalence, the poor prognosis, and the lack of effective treatment options, a substantial need exists for the development of agents for treating primary brain tumors.

SUMMARY OF THE INVENTION

A method of treating a primary brain tumor comprising administering to a patient in need thereof a therapeutically effective amount of letrozole is provided herein.

Also provided herein is a method of treating a primary brain tumor comprising (a) obtaining a biopsy of the primary brain tumor; (b) analyzing the biopsy to determine whether the primary brain tumor is a type of tumor that is responsive to letrozole treatment; and (c) administering a therapeutic amount of letrozole when the primary brain tumor is determined to be a type of tumor that is responsive to letrozole treatment.

These and other objects, features, embodiments, and advantages will become apparent to those of ordinary skill in the art from a reading of the following detailed description and the appended claims.

DETAILED DESCRIPTION OF THE INVENTION

Figure 1:
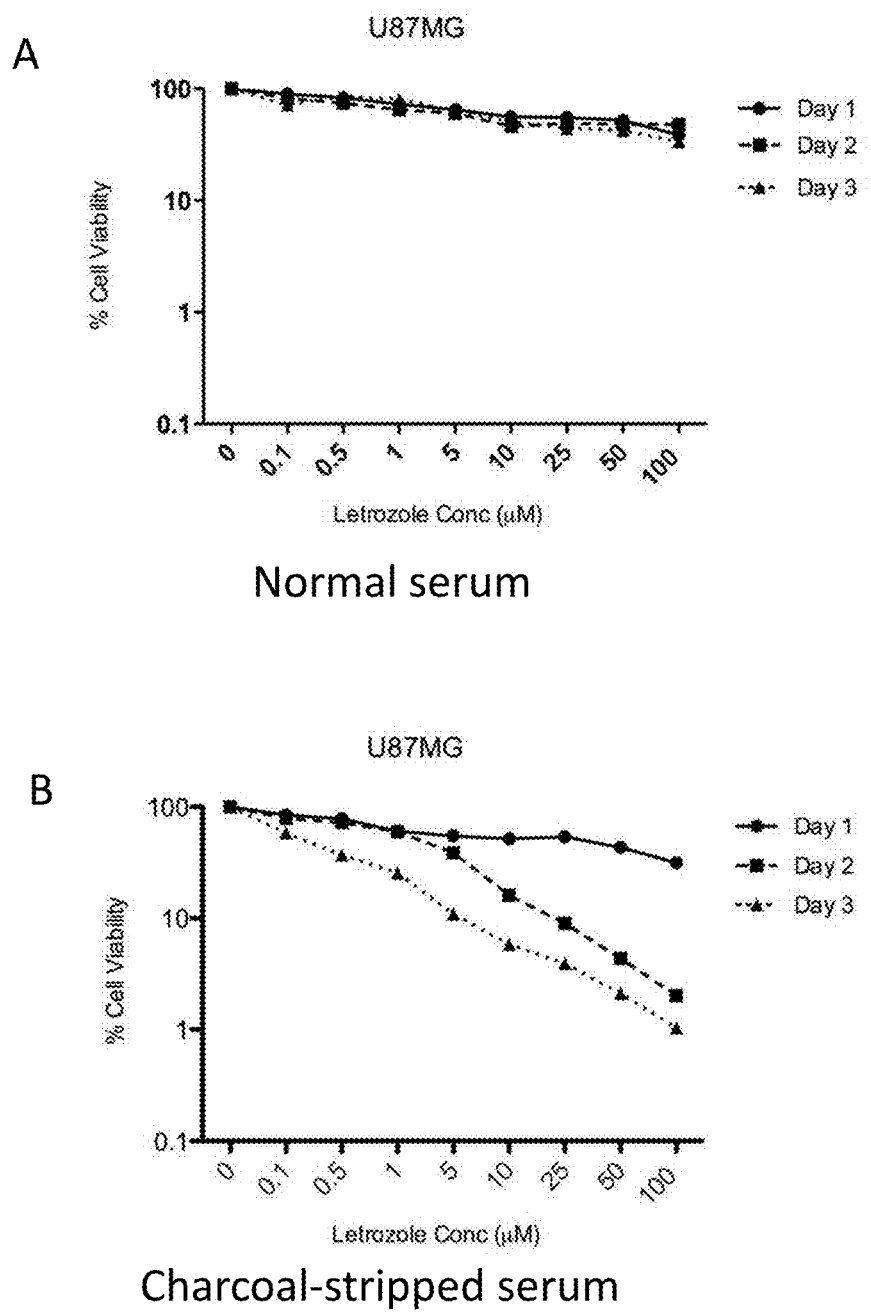
FIG. 1. Concentration and time-dependent cytotoxicity of letrozole in human glioma cell line U87MG in cell culture medium containing (A) normal serum, (B) charcoal-stripped serum.

The details of one or more embodiments of the presently-disclosed subject matter are set forth in this document. Modifications to embodiments described in this document, and other embodiments, will be evident to those of ordinary skill in the art after a study of the information provided in this document.

While the following terms are believed to be well understood by one of ordinary skill in the art, definitions are set forth to facilitate explanation of the presently-disclosed subject matter.

Unless defined otherwise, all technical and scientific terms used herein have the same meaning as commonly understood by one of ordinary skill in the art to which the presently-disclosed subject matter belongs.

Unless otherwise indicated, all numbers expressing quantities of ingredients, properties such as reaction conditions, and so forth used in the specification and claims are to be understood as being modified in all instances by the term "about." Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

As used herein, the terms "treatment" or "treating" of a condition and/or a disease in an individual, including a human or lower mammal, means:

(i) preventing the condition or disease, that is, avoiding any clinical symptoms of the disease, particularly in individuals at risk for developing the condition or disease;

(ii) inhibiting the condition or disease, that is, arresting the development or progression of clinical symptoms; and/or (iii) relieving the condition or disease, that is, causing the regression of clinical symptoms.

The term "therapeutically effective amount" as defined herein in relation to the treatment of primary brain tumors refers to an amount that will decrease, reduce, inhibit, or otherwise abrogate the growth of a cancer cell or tumor. The specific therapeutically effective amount will vary with such factors as the particular disease being treated, the physical condition of the individual being treated, the duration of the treatment, the nature of concurrent therapy (if any), and the specific formulations employed.

In premenopausal women, the majority of estrogen is produced in the ovaries, which is regulated by pituitary gonadotropins. Only a small portion of the estrogen is derived from the adrenal gland. In postmenopausal women, estrogen production in the ovaries ceases, but estrogen continues to be produced from androgens by aromatase enzyme in peripheral tissue. Many breast cancers (approximately 75%) are estrogen receptor positive (ER+) tumors, meaning that the tumor cells grow in response to the hormone estrogen.

Aromatase is a member of cytochrome P450 superfamily (CYP19) proteins residing in the endoplasmic reticulum. Aromatase catalyzes the conversion of estrogen from androgens by aromatization of the A-ring, transforming androstenedione to estrone and testosterone to estradiol. The aromatase enzyme is expressed in many tissues, including gonads, brain, adipose tissue, placenta, blood vessels, skin, bone, and endometrium, as well as in tissues of breast cancer, endometrial cancer, endometriosis, and uterine fibroids.

Aromatase inhibitors (AIs) have been successfully employed in treating certain postmenopausal ER+ breast tumors. AIs are classified as nonselective/irreversible/steroidal inhibitors and selective/reversible/nonsteroidal inhibitors. Testolactone was the first AI studied for the treatment of advanced breast tumors. Aminoglutethimide was another first generation AI found to be as efficacious as adrenolectomy. However, these first generation AIs were nonselective and, hence, also inhibited production of important mineralcorticoids and adrenocorticoids, necessitating concomitant use of steroids. Fadrozole and formestane were second generation AIs, which were less toxic than aminoglutethimide/testolactone, but their potency was unsatisfactory. Exemestane is a third generation AI that was more potent than first or second generation AIs, but still carried some of the adverse effects due to its steroidal structure. The third generation nonsteroidal AIs, anastrozole and letrozole, are much more potent and lack serious steroidal side effects.

However, AIs are effective breast cancer treatments only in postmenopausal women, in whom estrogen is produced predominantly in peripheral tissues (i.e. in adipose tissue, like that of the breast). In premenopausal women, the main source of estrogen is from the ovaries and not the peripheral tissues, and thus AIs are ineffective breast cancer therapies.

Letrozole is a non-steroidal aromatase inhibitor having the following chemical structure:

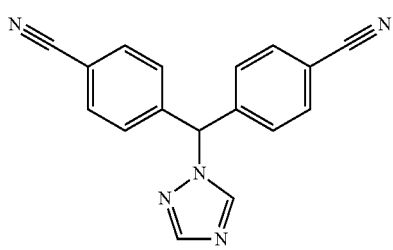 [SMILES: N#Cc1ccc(C(c2ccc(C#N)cc2)n2cncn2)cc1]

Letrozole is also known by the name 4,4'-((1H-1,2,4-triazol-1-yl)methylene)dibenzonitrile.

Cases have been reported wherein ER+ breast cancer patients with brain metastases responded to treatment with letrozole. In one instance, a 51-year-old postmenopausal female was treated for ER+ invasive ductal carcinoma of the right breast with radical mastectomy, anthracycline-based chemotherapy, and 5 yrs of tamoxifen. Approximately 10 years later, brain CT showed multiple brain metastases. The patient was initiated on letrozole therapy (2.5 mg daily) and 20 months later, complete recovery of neurological functions was observed as evident in CT scans showing calcification of cerebral lesions (Goyal et al., *Excellent response to letrozole in brain metastases from breast cancer*, Acta Neurochir (Wein) 150:613-14 (2008)). In another case, a 43-yr old woman with infiltrating ductal carcinoma of the right breast was treated in 2001 with anthracycline-based chemotherapy and continued oral 20 mg tamoxifen once daily therapy. In 2003, she had episodes of unconsciousness with right scalp swelling. Contrast-enhanced computed tomography (CECT) revealed brain and scalp metastasis. The swelling was managed with mannitol and corticosteroids and she was switched to 5-mg letrozole tablets, once daily. Repeat CECT in 2005 revealed complete resolution of scalp swelling and significant reduction in the brain metastases (Madhup et al., *Letrozole for brain and scalp metastases from breast cancer—a case report*, Breast 15:440-42 (2006)).

Surprisingly, the instant inventors have discovered that letrozole is effective in the treatment of primary brain tumors, including gliomas. This novel use for letrozole is indeed surprising, since primary brain tumor cells differ significantly from brain metastases from breast cancer. For example, metastatic ER+ breast cancer cells may retain the ER+ and aromatase (CYP19) positive features of breast carcinoma which make ER+ breast cancers selectively susceptible to aromatase inhibitors. However, in the case of primary brain tumors such as gliomas, aromatase expression has not previously been recognized as a viable selective target for primary brain tumor growth or development. Although aromatase is expressed in various types of cells throughout the body, including the brain, in order to be a viable target for a cancer therapy, aromatase must be overexpressed such that it provides for a selective target of the primary brain tumor cells over normal brain tissue. Surprisingly, the instant findings show that aromatase inhibition is a means of selectively targeting primary brain tumor cells.

However, primary brain tumors are especially difficult to treat, given the brain's natural defenses (BBB) and the tumor's defenses (BTB), which prevent many otherwise effective therapeutics from accessing cancer cells. In the case of brain metastases, the BBB is typically disrupted, which provides easier access of drugs to the metastatic brain tumor. Conversely, primary brain tumors are much better protected and the BBB and BTB remain substantially intact. Indeed, certain primary brain tumors develop mechanisms of resistance to keep therapeutic drugs out by expressing efflux pumps that prevent drugs from crossing the BTB. The presence of the BTB in primary brain tumors is a substantial factor in the failure of chemotherapeutic agents and skilled artisans acknowledge that whether a drug will effectively cross the BBB/BTB remains unpredictable.

Surprisingly, the present inventors have further found that letrozole is able to cross both the BBB and the BTB in order to reach primary malignant tumors in the brain. The current findings show, for the first time, the effectiveness of letrozole in crossing the BBB and BTB in order to penetrate and selectively target primary brain tumors.

Accordingly, provided herein is a method of treating a primary brain tumor comprising administering to a patient in need thereof a therapeutically effective amount of letrozole. The methods disclosed herein are useful for treating a variety of primary brain tumors. In one embodiment, the primary brain tumor is selected from the group consisting of glioma, meningeal tumor, medulloblastoma, and schwannoma. The skilled artisan will appreciate that certain types of primary brain tumors are further differentiated into various subtypes, which may also be further differentiated into subtypes or grades. For example, in certain embodiments, the primary brain tumor is a glioma selected from the group consisting of astrocytoma, oligodendroma, and ependymoma. In a more specific embodiment, the primary brain tumor is an astrocytoma selected from the group consisting of Grade I, Grade II, Grade III, and Grade IV. In another embodiment, the primary brain tumor is a meningeal tumor selected from the group consisting of meningioma, atypical meningioma, anaplastic or malignant meningioma, hemangiopericytoma, anaplastic hemangiopericytoma, and hemangioblastoma.

The therapeutically effective amount of letrozole refers to an amount that will decrease, reduce, inhibit, or otherwise abrogate the growth of a primary cancer cell or tumor in the brain. The specific therapeutically effective amount will vary with such factors as the particular disease being treated, the physical condition of the individual being treated, the duration of the treatment, the nature of concurrent therapy (if any), and the specific formulations employed. In some embodiments, letrozole can be administered regionally, i.e., directly to a particular affected region or regions of the patient's brain. In some embodiments, where such treatment is deemed more suitable, letrozole can be administered systemically. For example, letrozole can be administered via oral, intravenous, subcutaneous, intramuscular, intraperitoneal, sublingual, rectal, pulmonary, or nasal routes of delivery. In a specific example, letrozole is administered orally or intravenously. In other embodiments, where such treatment is deemed more suitable, letrozole can be administered topically. Advantageously, letrozole effectively crosses the blood brain barrier (BBB) and the blood tumor barrier (BTB) in order to therapeutically treat primary brain tumors.

In one embodiment, the therapeutically effective amount of letrozole comprises a daily dose of from about 1 mg to about 1000 mg. In another embodiment, the therapeutically effective amount of letrozole comprises a daily dose of from about 1 mg to about 100 mg. In another embodiment, the therapeutically effective amount of letrozole comprises a daily dose of from about 1 mg to about 75 mg. In a specific embodiment, the therapeutically effective amount of letrozole comprises a daily dose of from about 2.5 mg to about 60 mg.

In addition, it will be appreciated that therapeutic benefits can be realized by combining treatment of letrozole with one or more additional anti-cancer agents, adjuvants, or treatments. The choice of such combinations will depend on various factors including, but not limited to, the type of disease, age and general health of the patient, the aggressiveness of disease progression, and the ability of the patient to tolerate the agents that comprise the combination. For example, letrozole can be combined with other agents and therapeutic regimens that are effective at reducing tumor size (e.g., radiation, surgery, chemotherapy, hormonal treatments, and/or gene therapy). In some embodiments, it may be desirable to combine letrozole with one or more agents that treat the side effects of a disease or the side effects of one of the therapeutic agents, e.g., providing the patient with an analgesic, or agents effective to stimulate the patient's own immune response.

A variety of chemical compounds can be used in combination with letrozole. Such compounds include, but are not limited to, chemotherapeutic agents, anti-inflammatory agents, immunosuppressive agents, and corticosteroids. Specific examples of chemotherapeutic agents include, but are not limited to, alkylating agents, platinum drugs, antimetabolites, anti-tumor antibiotics, topoisomerase inhibitors, mitotic inhibitors, targeted therapies, anti-angiogenic compounds, differentiating agents, hormone therapies, and the like.

Suitable alkylating agents include, but are not limited to, (1) nitrogen mustards: such as mechlorethamine, chlorambucil, cyclophosphamide, ifosfamide, and melphalan; (2) nitrosoureas: such as streptozocin, carmustine (BCNU), which may be used for local therapy (for example as Gliadel® wafers), and lomustine; (3) alkyl sulfonates, such as busulfan; (4) triazines, such as dacarbazine (DTIC) and temozolomide; and (5) ethylenimines, such as, thiotepa and altretamine (hexamethylmelamine).

Suitable platinum drugs include, but are not limited to, cisplatin, carboplatic, and oxalaplatin.

Suitable antimetabolites include, but are not limited to, 5-fluorouracil (5-FU), 6-mercaptopurine (6-MP), capecitabine, cladribine, clofarabine, cytarabine, floxuridine, fludarabine, gemcitabine, hydroxyurea, methotrexate, premetrexed, pentostatin, and thioguanine.

Suitable anti-tumor antibiotics include, but are not limited to, anthracyclines, such as daunorubicin, doxorubicin, epirubicin, idarubicin, and mitoxantrone; and other anti-tumor antibiotics such as actinomycin-D, bleomycin, and mitomycin-C.

Suitable topoisomerase inhibitors include, but are not limited to, topotecan and irinotecan (CPT-11) and topoisomerase II inhibitors such as etoposide (VP-16), teniposide, and mitoxantrone.

Suitable mitotic inhibitors include, but are not limited to, taxanes, such as paclitaxel (also referred to as taxol) and docetaxel; Epothilones such as ixabepilone; vinca alkaloids such as vinblastine, vincristine, vinorelbine, and estramustine.

Suitable targeted therapies include, but are not limited to, (1) small molecules, such as imatinib, gefitinib, nilotinib, lapatinib, sunitinib, and axitinib; (2) monoclonal antibodies, such as bevacizumab (Avastin®), alemtuzumab, cetuximab, rituximab, and trastuzumab; (3) PI3 kinase inhibitors, such as BEA235; and (4) inhibitors of the mammalian target of rapamycin (mTOR), such as everolimus, sirolimus, and tacrolimus.

Anti-angiogenic compounds suitable for combination with letrozole include, but are not limited to, axitinib, and bevacizumab (Avastin®).

Suitable differentiating agents include, but are not limited to, retinoids, tretinoin (ATRA or Atralin®), bexarotene (Targretin®), and arsenic trioxide (Arsenox®).

Hormone therapies suitable for combination with letrozole include, but are not limited to, anti-estrogens such as tamoxifen, toremifene, and fulvestrant.

Additional chemotherapeutic agents suitable for combination with letrozole include L-asparaginase and the proteosome inhibitor bortezomib.

Suitable corticosteroids include, but are not limited to, prednisone, methylprednisolone (Solumedrol®), and dexamethasone (Decadron®).

Letrozole may also be combined with certain devices or alternative therapies. For example, letrozole may be combined with therapies that employ electric fields to disrupt cell division (such as tumor treating fields (TTF) therapy by Novocure™). In another embodiment, letrozole may be combined with boron neutron capture therapy.

Combination treatments involving letrozole and another therapeutic agent can be achieved by co-administering the agents, i.e., contacting cells with letrozole and the other agent at the same time. Such combinations can be achieved by contacting the cell with a single composition or pharmaceutical formulation that includes both agents, or by contacting the cell with two distinct compositions or formulations, at the same time, wherein one composition includes letrozole and the other composition includes the other agent.

Alternatively, treatment with letrozole can precede or follow treatment with the other agent by intervals ranging from minutes to weeks. In embodiments where the other agent and letrozole are applied separately to the cell, one would generally ensure that a significant period of time did not expire between the time of each delivery, such that the agent and letrozole would still be able to exert an advantageously combined effect on the cell. In such instances, it is provided that one would contact the cell with both modalities within about 12-24 hours of each other and, optionally, within about 6-12 hours of each other. In some situations, it can be desirable to extend the time period for treatment significantly, however, where several days (2, 3, 4, 5, 6 or 7) to several weeks (1, 2, 3, 4, 5, 6, 7 or 8) lapse between the respective administrations. Also, under some circumstances, more than one administration of either letrozole and/or the other agent will be desired.

Additional cancer treatments also can be used in combination with administration letrozole. For example, letrozole can be used as part of a treatment course further involving attempts to surgically remove part or all of a cancerous growth. For instance, letrozole can be administered after surgical treatment of a patient to treat any remaining cancer cells. Treatment with letrozole can precede surgery, in an effort to shrink the size of a tumor to reduce the amount of tissue to be excised, thereby making the surgery less invasive and traumatic. Letrozole can also be administered during surgery, as a means of regionally administering the drug to the treatment area.

Treating primary brain tumors with letrozole can further include one or more treatment courses with a radiotherapeutic agent to induce DNA damage. Radiotherapeutic agents, include, for example, gamma irradiation, X-rays, UV-irradiation, microwaves, electronic emissions, radioisotopes, and the like. Therapy can be achieved by irradiating the localized tumor site with the above-described forms of radiation.

In another embodiment, it is useful to first biopsy a sample of a primary brain tumor to determine whether the tumor is responsive to letrozole prior to administering letrozole to the patient. Thus, provided herein is also a method of treating a primary brain tumor in a patient comprising (a) obtaining a biopsy of the primary brain tumor; (b) analyzing the biopsy to determine whether the primary brain tumor is a type of tumor that is responsive to letrozole treatment; and (c) administering a therapeutic amount of letrozole to the patient when the primary brain tumor is determined to be a type of tumor that is responsive to letrozole treatment.

EXAMPLES

The following examples are given by way of illustration and are in no way intended to limit the scope of the present invention.

Example 1

Aromatase Expression in Human and Rat Glioma Cell Lines

In vitro studies indicated that several human patient-derived glioma cell lines, including U87G, LN-229, U373MG, U251MG, T98G and rat glioma cell line C6, express CYP19 (aromatase). Results are shown in Table 1 below:

TABLE 1

Aromatase Expression in Human and Rat Glioma Cell Lines

| Glioma Cell line | Relative Expression of CYP19 |
|---|---|
| MCF-7 | 1 |
| MDA-MB-231 | 0.37 |
| C6 | 1.19 |
| LN229 | 1.25 |
| T98G | 1.35 |
| U373MG | 1.69 |
| U251MG | 2.03 |
| U87MG | 2.57 |

Expression of aromatase was confirmed by real time RT-PCR, using GAPDH as the endogenous control. MCF-7, estrogen receptor positive (ER+) breast cancer cell line was used as a positive control (Cos et al., 2005) and triple-negative breast cancer cell-line, MDA-MB-231 was used as a negative control. Aromatase expression was represented relative to that of the positive control, MCF-7 cell line. The relative aromatase expression was 1.19 for the rat glioma cell line C6 and ranged from 1.15 to 2.57 for human glioma cell lines. Results show that the tested glioma cell lines express higher levels of aromatase compared to the breast cancer cell line MCF-7.

Example 2

Time- and Dose-Dependent Cytotoxicity of Letrozole

Figure 2:
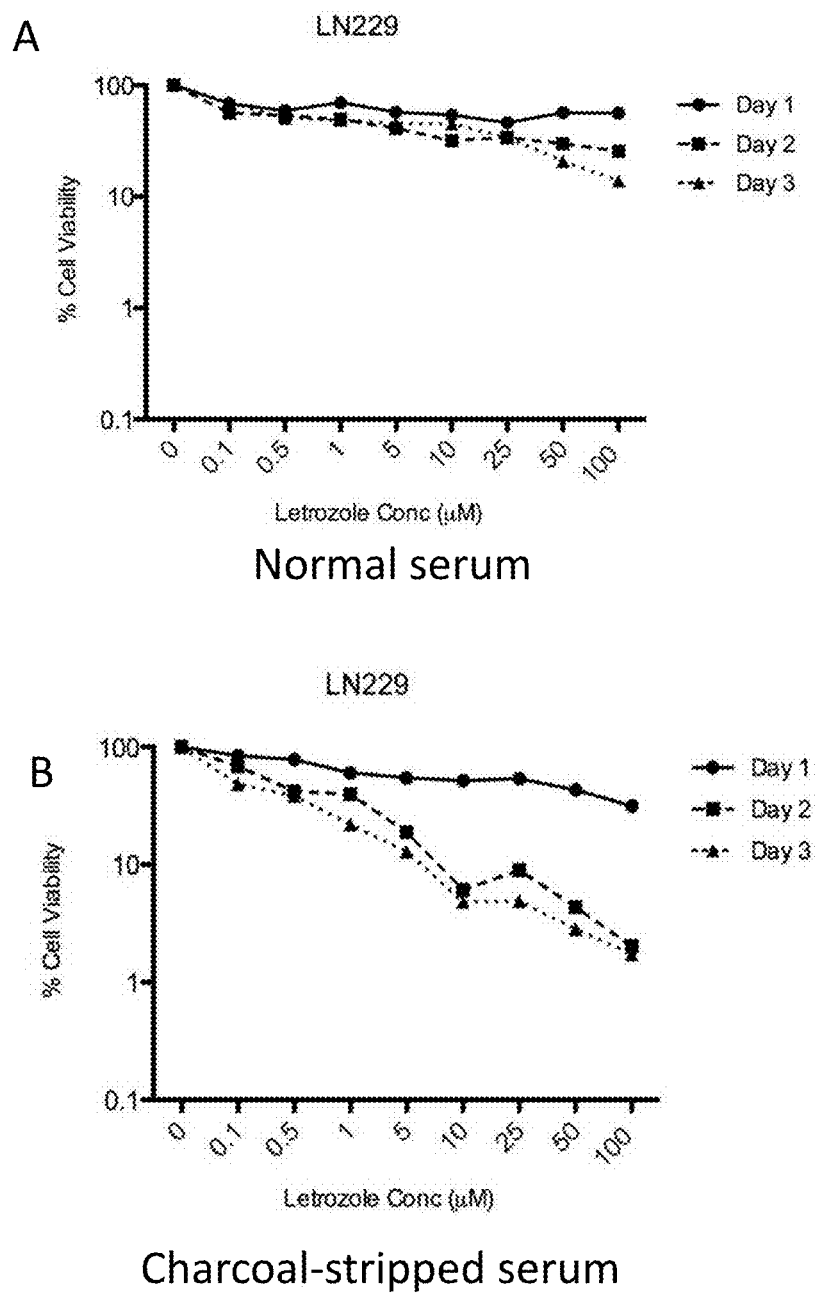
FIG. 2. Concentration and time-dependent cytotoxicity of letrozole in human glioma cell line LN229 in cell culture medium containing (A) normal serum, (B) charcoal-stripped serum.
Figure 3:
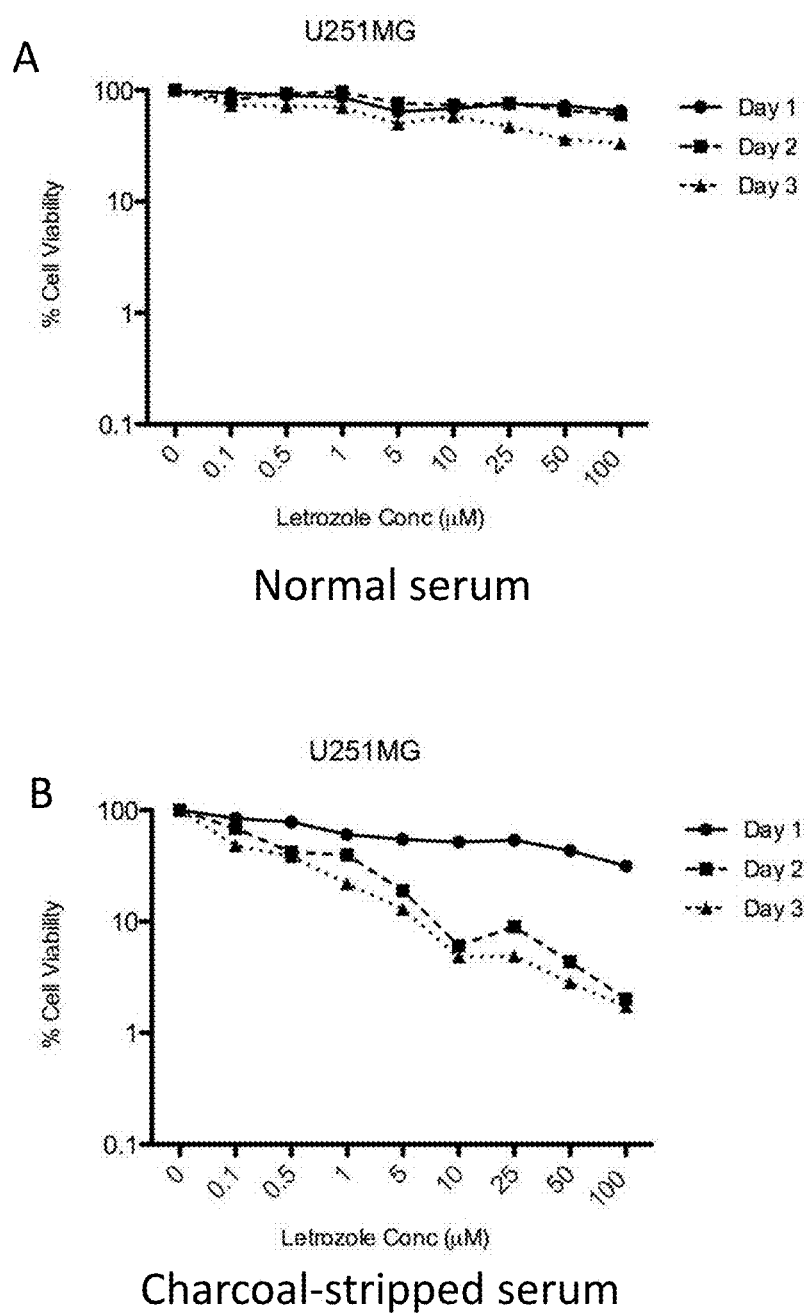
FIG. 3. Concentration and time-dependent cytotoxicity of letrozole in human glioma cell line U251MG in cell culture medium containing (A) normal serum, (B) charcoal-stripped serum.

Time- and dose-dependent cytotoxicity of letrozole was evaluated in the cell lines expressing CYP19. Letrozole concentrations ranging from 0-100 µM were tested. Cells were incubated with drug for 1-3 days. Cytotoxicity of letrozole was higher in cell culture media containing charcoal-stripped serum (absence of steroids, including estrogen) as compared to normal serum, as shown for U87MG, LN229, and U251MG, in FIGS. 1-3, respectively.

Figure 4:
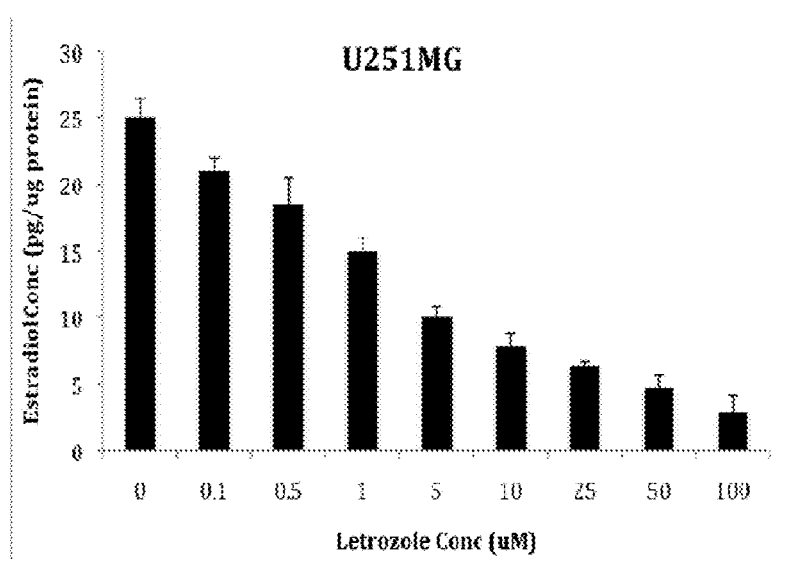
FIG. 4. Concentration-dependent inhibition of aromatase activity by letrozole in human glioma cell line U251MG.
Figure 5:
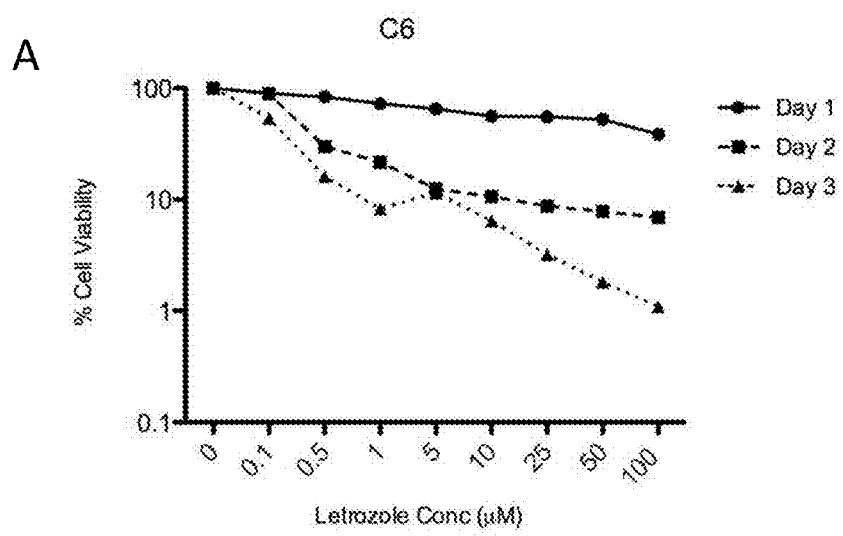
FIG. 5. (A) Concentration and time-dependent cytotoxicity of letrozole in rat glioma cell line C6 in cell culture medium containing charcoal-stripped serum. (B) Concentration-dependent inhibition of aromatase activity by letrozole in rat glioma cell line C6.
Figure 5:
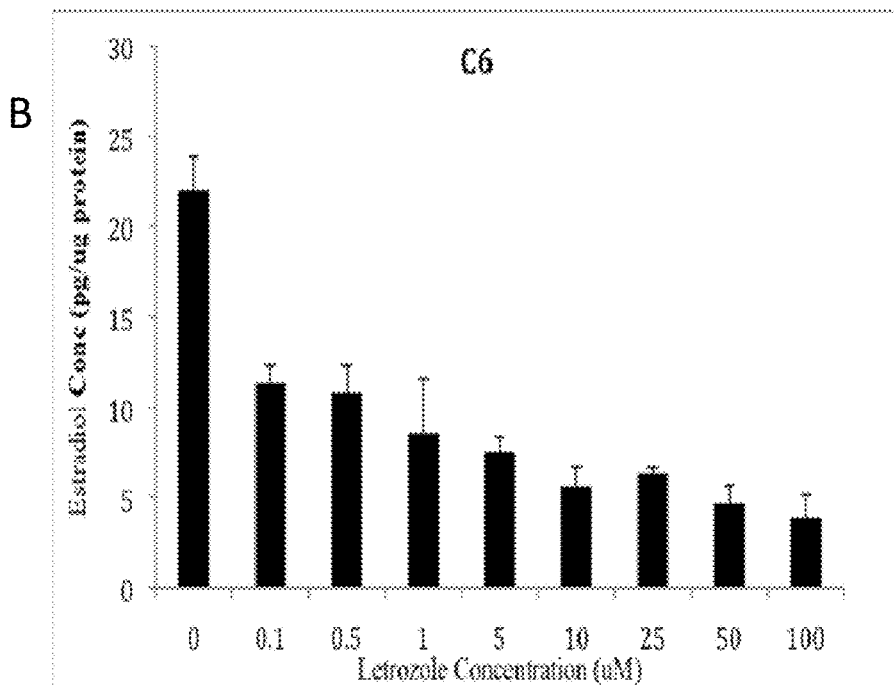
Figure 6:
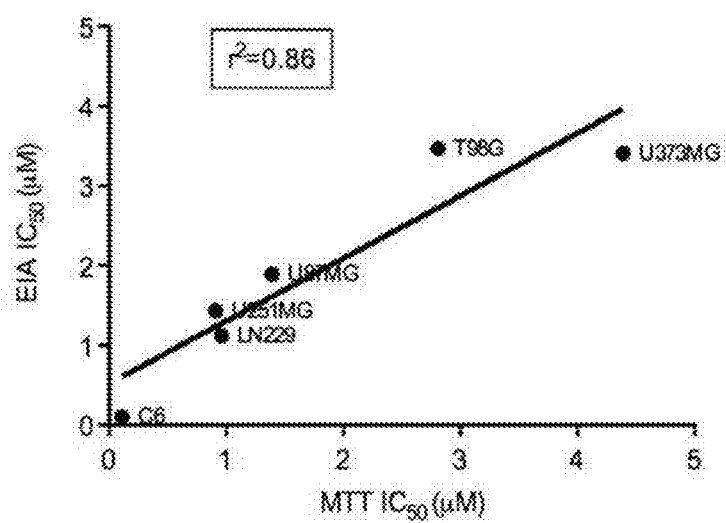
FIG. 6. Correlation between observed cytotoxicity (MTT assay) and inhibition of aromatase activity (EIA assay).

In order to confirm that the observed cytotoxicity of letrozole is due to inhibition of aromatase, aromatase activity was assessed in cells incubated with letrozole, at concentrations ranging from 0-100 µM. Since aromatase converts testosterone to estradiol, testosterone substrate (0.1 µM) was added together with letrozole. After 2 days incubation, estradiol concentrations were measured using an estradiol ELISA kit, indirectly measuring aromatase activity. Results indicate that letrozole decreased aromatase activity, which in turn decreased estradiol formation. FIG. 4 shows concentration-dependent inhibition of aromatase activity by letrozole in human glioma cell line U251MG. FIG. 5 shows cytotoxicity via MTT assay (A) and aromatase activity via EIA assay (B) results in C6 rat glioma cell line. Results indicate excellent correlation ($R^2=0.86$) between dose-dependent decrease of aromatase activity and cytotoxicity (Table 2, FIG. 6), indicating that cell proliferation may depend on formation of estradiol from testosterone via aromatase activity of the cells.

TABLE 2

$IC_{50}$ values for observed cytotoxicity (MTT assay) and aromatase activity (EIA assay)

| Cell line | $IC_{50}$ (µM) (MTT) | $IC_{50}$ (µM) (EIA) |
|---|---|---|
| MCF-7 | <0.1 | <0.1 |
| MDA-MB-231 | >100 | >100 |
| C6 | 0.11 | 0.1 |
| LN229 | 0.96 | 1.12 |
| T98G | 2.81 | 3.47 |
| U373MG | 4.39 | 3.41 |
| U251MG | 0.91 | 1.43 |
| U87MG | 1.39 | 1.89 |

Example 3

Pharmacokinetic Analysis of Letrozole

The pharmacokinetic profile of letrozole in normal brain and brain tumor relative to its plasma pharmacokinetics at different dose strengths was analyzed.

Experiments were carried out in female Sprague-Dawley rats weighing 200-250 g. The technique of intracerebral microdialysis was employed, which measures unbound drug concentrations in the extracellular fluid (ECF) and has been demonstrated to be an effective tool to monitor drug concentrations in the selected regions of the brain over time. Blood samples from jugular vein cannulation and dialysate samples from microdialysis probe implanted stereotactically into the striatum region of the brain were obtained every 30 minutes over 8 hours and analyzed by HPLC (fluorescence detection, Excitation λ, 230 nm; Emission λ, 295 nm). Microdialysate samples were corrected for in vivo relative recovery (9.5%), measured under similar experimental conditions.

In order to obtain the correct ECF concentrations from those obtained by bioanalysis of dialysate samples, the correction factor known as "% recovery" is employed. The % recovery for a compound can be obtained by in vivo or in vitro recovery analysis. For in vitro recovery analysis, efficiency of the microdialysis probe was determined by immersing probes in reservoirs containing solutions of letrozole (1/5/10 µM) in an enclosed environment at 37° C. Probes were perfused with physiological buffer and dialysate samples were collected every 30 minutes over 6 hours and analyzed for letrozole. In vitro relative recovery was calculated as follows:

$$\% \text{ recovery}_{in\ vitro} = [C_{(dialysate)}/C_{(reservoir)}] \times 100$$

For in vivo recovery analysis, retrodialysis was employed to estimate the in vivo recovery of letrozole in rats. The perfusion buffer contained known concentrations of letrozole (10 or 25 μM). Following equilibration for 1 hr, dialysis samples were collected every 30 min for 6 hours. % loss of letrozole calculated according to the following formula represents in vivo recovery, wherein $C_{(inlet)}$ is the concentration of letrozole in the inlet buffer and $C_{(outlet)}$ is the concentration in the dialysate buffer:

$$\% \text{ loss} = [(C_{(inlet)} - C_{(outlet)})/C_{(inlet)}] \times 100$$

The in vitro % recovery was average 8%, whereas the in vivo recovery was 9.5%. It was observed that the recovery of letrozole was independent of the concentration and was constant over the entire sampling time period of 8 hours.

For tumoral pharmacokinetic studies, C6 glioma cells (6×10⁶ cells) were injected orthotopically into the right striatum region of the brain (left striatum served as a control) and allowed to grow for 10 days before administration of letrozole followed by collection of microdialysis samples from both left and right striata. Microdialysis allows for determination of drug levels in freely moving rats. At the end of microdialysis, brain tissues were collected after transcardial perfusion for histological evaluation to confirm formation of tumor in the right striatum and immunohistochemistry to differentiate the expression of aromatase in tumoral and normal brain regions. The pharmacokinetic parameters (including time required to achieve maximum drug levels ($T_{max}$), area under the concentrations-time curve (AUC) over a defined time interval, and peak or maximum concentrations ($C_{max}$)) of both plasma and brain ECF were estimated by non-compartmental analysis using WinNonlin 6.2 (Pharsight Inc.).

Results show that letrozole effectively crosses the BBB and BTB and attains exposure (adequate concentrations and duration/persistence) above concentrations required to kill cancer cells.

Example 4

Normal Brain Versus Plasma Pharmacokinetics

Figure 7:
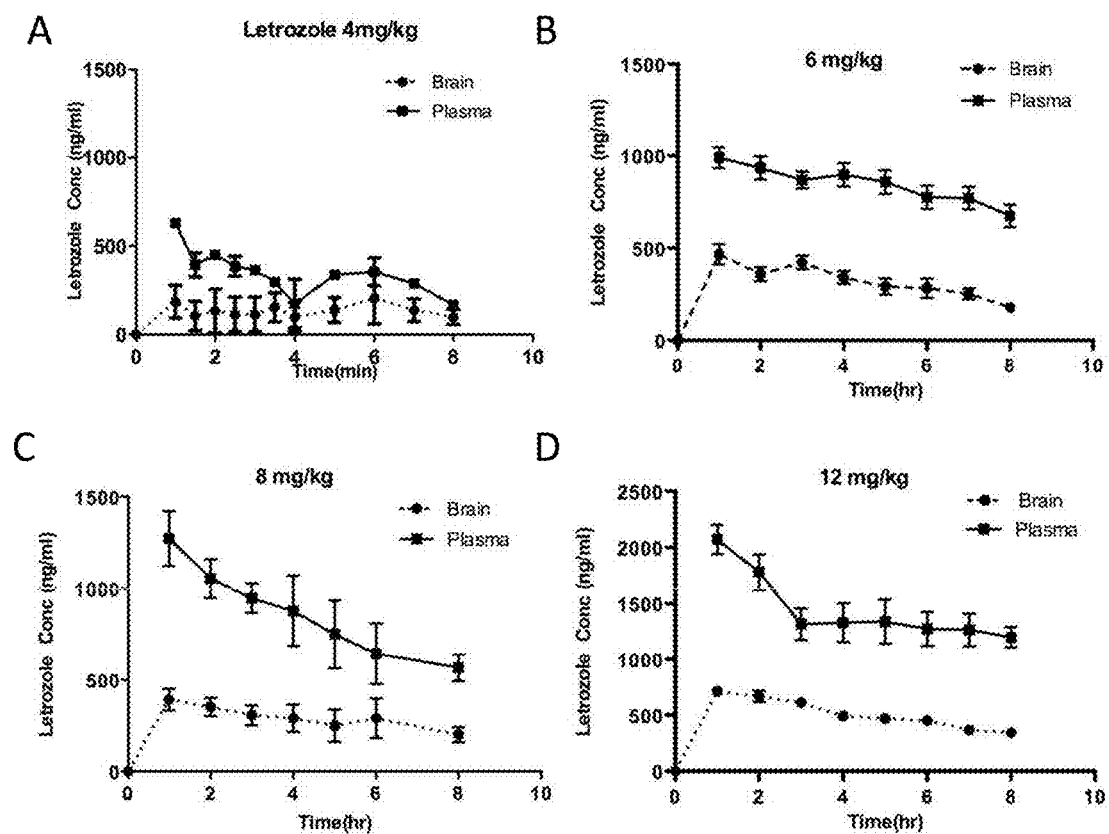
FIG. 7. Brain versus plasma letrozole levels during varying doses of letrozole IV bolus administration in female Sprague-Dawley rats. (A) Letrozole dose=4 mg/kg. (B) Letrozole dose=6 mg/kg. (C) Letrozole dose=8 mg/kg. (D) Letrozole dose=12 mg/kg. Data are presented as mean±SD.

The brain ECF concentrations were time-averaged over the collection interval and corrected for in vivo recovery. The normal brain ECF and plasma pharmacokinetic profiles of letrozole at doses of 4, 6, 8 and 12 mg/kg are shown in FIG. 7(A-D). The pharmacokinetic parameters are summarized in Table 3, which shows brain versus plasma pharmacokinetic parameter estimates after intravenous (IV bolus) administration of 4, 6, 8, and 12 mg/kg doses of letrozole in female Sprague-Dawley rats obtained by non-compartmental analysis. Results are presented as mean±SD. (N=9 for 4 and 8 mg/kg, N=6 for 6 and 12 mg/kg). As can be seen from the concentration-time profiles and the estimated $T_{max}$ values that ranged from 1.3-1.5 hrs, letrozole rapidly penetrated the BBB following intravenous bolus administration. Plasma protein binding with non-specific binding (NSB) correction was estimated to be 62% for concentration range 0.1-10 μM. Simultaneous plasma and ECF pharmacokinetic determination facilitated estimation of the relative brain distribution coefficient, calculated as ($AUC_{brain\ ecf}/AUC_{plasma,\ ub}$). At the dose of 4 mg/kg, the distribution coefficient was 0.32 but at all other doses it was relatively similar, ranging from 0.77-0.98 (Table 3).

TABLE 3

Brain versus Plasma Pharmacokinetics

| PK Parameter | Brain | Plasma$_{total}$ (Total) | Plasma$_{ub}$ (Unbound) | Ratio (Brain/ Plasma$_{ub}$) |
|---|---|---|---|---|
| Dose = 4 mg/kg | | | | |
| $T_{max}$ (hr) | 1.4 ± 0.6 | | | |
| $C_{max}$ (ng/ml) | 132 ± 79 | 682 ± 24 | 259 ± 9 | 0.51 |
| $AUC_{0-8\ hr}$ (h · ng/ml) | 583 ± 189 | 4782 ± 932 | 1817 ± 354 | 0.32 |
| Dose = 6 mg/kg | | | | |
| $T_{max}$ (hr) | 1.5 ± 0.7 | | | |
| $C_{max}$ (ng/ml) | 341 ± 8 | 916 ± 71 | 348 ± 27 | 0.98 |
| $AUC_{0-8\ hr}$ (h · ng/ml) | 2012 ± 137 | 5978 ± 146 | 2272 ± 56 | 0.89 |
| Dose = 8 mg/kg | | | | |
| $T_{max}$ (hr) | 1.33 ± 0.5 | | | |
| $C_{max}$ (ng/ml) | 376 ± 61 | 1277 ± 182 | 485 ± 69 | 0.77 |
| $AUC_{0-8\ hr}$ (h · ng/ml) | 2637 ± 286 | 8828 ± 1084 | 3355 ± 412 | 0.79 |
| Dose = 12 mg/kg | | | | |
| $T_{max}$ (hr) | 1.4 ± 0.6 | | | |
| $C_{max}$ (ng/ml) | 631 ± 22 | 2072 ± 258 | 787 ± 98 | 0.80 |
| $AUC_{0-8\ hr}$ (h · ng/ml) | 2547 ± 173 | 8059 ± 1419 | 3062 ± 539 | 0.83 |

Figure 8:
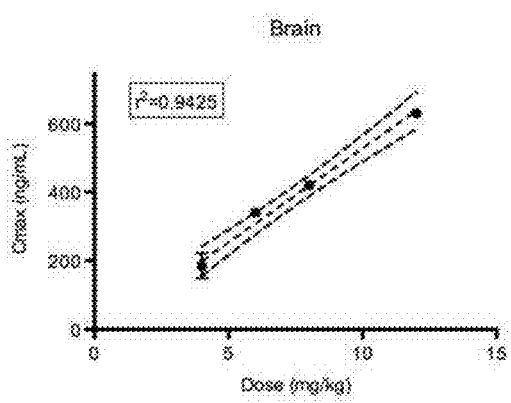
FIG. 8. Relationships of observed $C_{max}$ and $AUC_{(0-8\ hr)}$ values for letrozole concentrations in the brain and plasma versus letrozole IV bolus doses (4, 6, 8 and 12 mg/kg) with linear regression (bold line), and the 95% confidence interval (dashed line). (A) shows $C_{max}$ v. Dose in the brain, $r^2=0.9425$; (B) shows AUC v. Dose in the brain, $r^2=0.5426$; (C) shows $C_{max}$ v. Dose in the plasma, $r^2=0.9368$; (D) shows AUC v. Dose in the plasma, $r^2=0.8020$.
Figure 8:
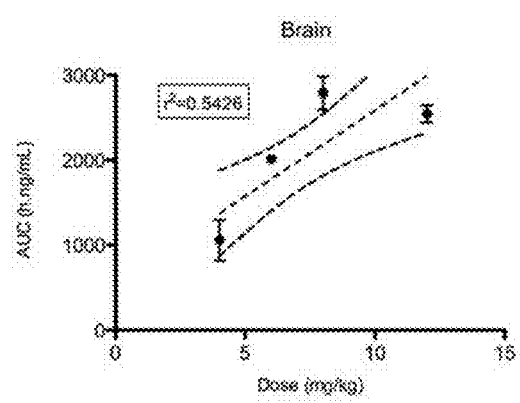
Figure 8:
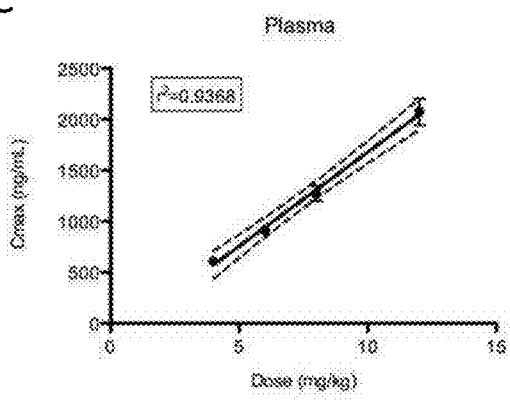
Figure 8:
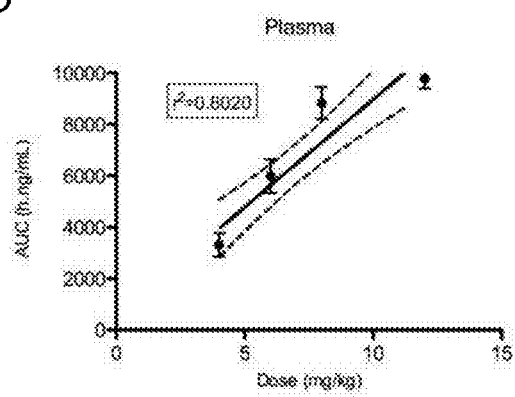
Figure 9:
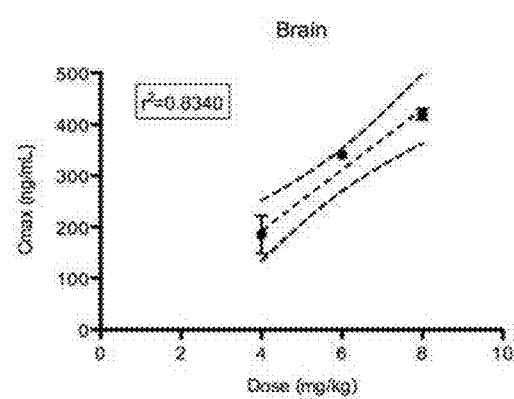
FIG. 9. Relationships of observed $C_{max}$ and $AUC_{(0-8\ hr)}$ values for letrozole concentrations in the brain and plasma versus letrozole IV bolus doses (4, 6, and 8 mg/kg) with linear regression (bold line), and the 95% confidence interval (dashed line). (A) shows $C_{max}$ v. Dose in the brain, $r^2=0.8340$; (B) shows AUC v. Dose in the brain, $r^2=0.8062$; (C) shows $C_{max}$ v. Dose in the plasma, $r^2=0.8961$; (D) shows AUC v. Dose in the plasma, $r^2=0.8619$.
Figure 9:
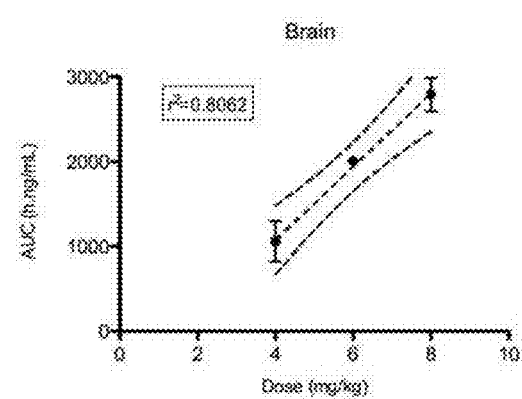
Figure 9:
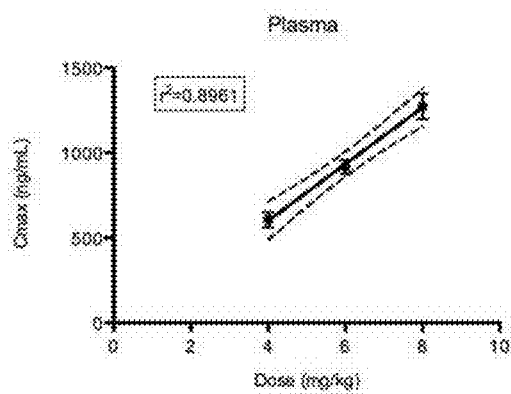
Figure 9:
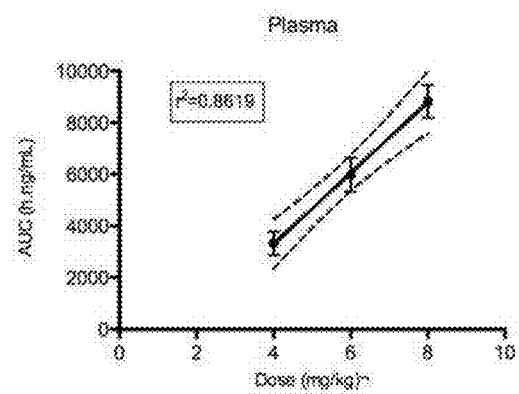

The relationship between brain ECF and plasma letrozole concentrations was examined using linear regression analysis (FIG. 8). At higher dose (12 mg/kg), brain and plasma $C_{max}$ maintained linearity ($r^2$=0.9425 and 0.9368 for brain ECF and plasma respectively, FIG. 8(A), 8(C)). However, $AUC_{0-8hr}$ for both brain and plasma showed non-linearity at 12 mg/kg ($r^2$=0.5426 and 0.8220 for brain ECF and plasma respectively, FIG. 8(B), 8(D)). Both brain ECF and plasma $C_{max}$ increased linearly with increase in letrozole doses of 4, 6 and 8 mg/kg ($r^2$=0.8340 and 0.8961 for brain ECF and plasma, respectively, FIG. 9(A), 9(C)). Similarly, $AUC_{0-8hr}$ for both brain and plasma showed linearity over doses 4, 6 and 8 mg/kg ($r^2$=0.8062 and 0.8619 for brain ECF and plasma, respectively, FIG. 9(B), 9(D)). Thus, it appears that brain and plasma pharmacokinetics are linear up to 8 mg/kg and potentially non-linear thereafter.

While not desiring to be bound by theory, it is believed that the proportional correlation between an increase in dose and both systemic drug exposure and brain exposure indicates that letrozole transport to the brain is unlikely to be mediated or impacted by an active transport mechanism.

Example 5

Tumoral Versus Normal Brain Pharmacokinetics

Figure 10:
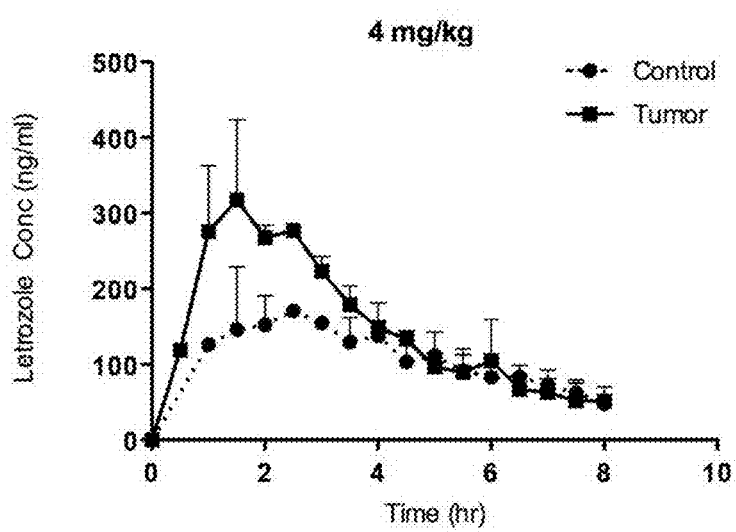
FIG. 10. Normal (Control) versus tumoral brain letrozole levels during varying doses of letrozole IV bolus administration in female Sprague-Dawley rats. (A) Letrozole dose=4 mg/kg. (B) Letrozole dose=8 mg/kg. Data presented as mean±SD.
Figure 10:
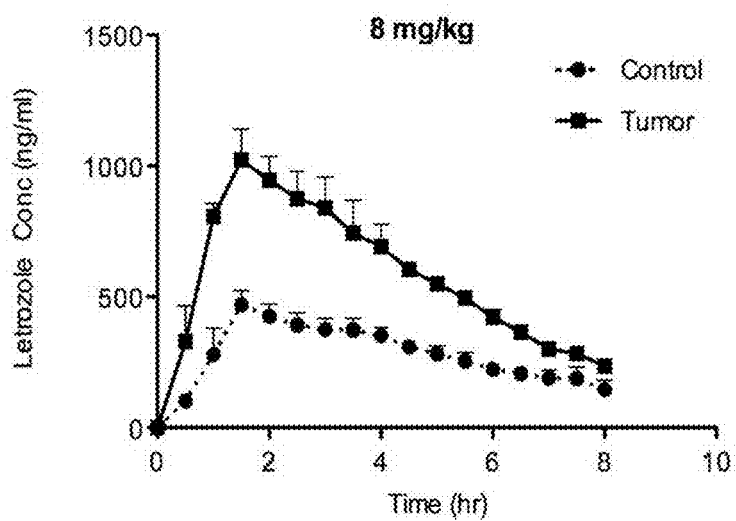

Following tumor implantation (see Example 3), all animals resumed normal activity and no major physiological changes were observed during the 10-day period of tumor growth. Histology of rat brains was performed as outlined in Apparaju et al., *Pharmacokinetics of gemcitabine in tumor and non-tumor extracellular fluid of brain: an in vivo assessment in rats employing intracerebral microdialysis, Cancer Chemother. Pharmacol.* 61: 223-29 (2008). Tumor volume ranged from 100-150 mm³ at the site of implantation in the right striatum. Brain ECF concentrations versus time profiles of letrozole in the tumor- and tumor-free brain regions of glioma-bearing rats are shown in FIG. 10. Estimated pharmacokinetic parameters are summarized in Table 4, showing normal vs. tumoral brain pharmacokinetic parameter estimates after IV bolus administration of 4 mg/kg and 8 mg/kg doses of letrozole in female Sprague-Dawley rats, obtained by non-compartmental analysis. Results are presented as mean±SD (n=6).

TABLE 4

Normal versus Tumoral Brain Pharmacokinetic Parameter Estimates

| PK Parameter | Control | Tumor | Ratio (Tumor/Control) |
|---|---|---|---|
| A. Dose = 4 mg/kg | | | |
| $T_{max}$ (hr) | 1.75 ± 0.5 | 1.5 ± 0 | |
| $C_{max}$ (ng/ml) | 183 ± 13 | 354 ± 34 | 1.93 |
| $AUC_{0-8\ hr}$ (h · ng/ml) | 803 ± 216 | 1163 ± 167 | 1.45 |
| B. Dose = 8 mg/kg | | | |
| $T_{max}$ (hr) | 1.33 ± 0.3 | 1.5 ± 0 | |
| $C_{max}$ (ng/ml) | 475 ± 87 | 1022 ± 204 | 2.15 |
| $AUC_{0-8\ hr}$ (h · ng/ml) | 2276 ± 428 | 4700 ± 555 | 2.07 |

As shown, letrozole ECF concentrations in tumoral region were considerably higher than that in the contralateral tumor-free region of the brain. The $AUC_{0-8hr}$ of the tumor brain region was approximately 1.5-2.0 folds higher relative to tumor-free region for the two doses of letrozole, 4 and 8 mg/kg (P<0.05). The pharmacokinetic parameters of control brain regions in tumor-bearing rats were similar to those in normal brain versus plasma study at the same doses. Results indicate that letrozole shows increased permeability only in tumoral regions of the brain.

Histological evaluation (data not shown) indicated that tumor mass was restricted to the right hemisphere with no spread to the left hemisphere, which served as a control. The placement of the microdialysis probe was confirmed by microscopic examination, showing a narrow path formed by the probe in the tumor mass.

Results indicate that exposure of letrozole after administration of a single dose is efficacious in vivo. Results further indicate that letrozole has the required pharmacokinetic properties (penetration from blood circulation to the tumoral milieu) to be effective against primary brain tumors.

Example 6

In Vivo Anti-Tumor Efficacy Study of I.V. Dosed Letrozole in Rats with Tumor Allografts Anti-tumor efficacy of letrozole in a rat model was analyzed. μPET/CT was employed to measure tumor volumes before and after letrozole treatment. 10 days after tumor implantation, anesthetized rats were scanned on μPET scanner (Siemens Inveon) to obtain active tumor volume at Day 0. Rats were then injected 0.4 ml/kg/day vehicle for control untreated group and 4 mg/kg/day letrozole for treatment group by intravenous bolus injection for 8-10 days. μPET/CT scans were obtained again on day 5 and/or day 8/10 after treatment as before and active tumor volumes were obtained.

Figure 11:
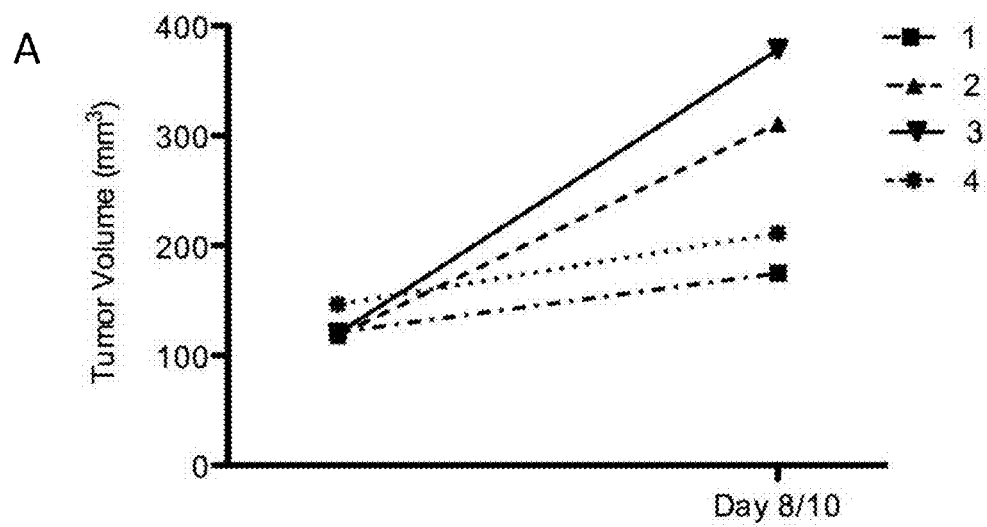
FIG. 11. Change in active tumor volume for (A) control group (0.4 ml saline Day 1-8, n=4) and (B) treatment group (4 mg/kg/day i.v., n=8).
Figure 11:
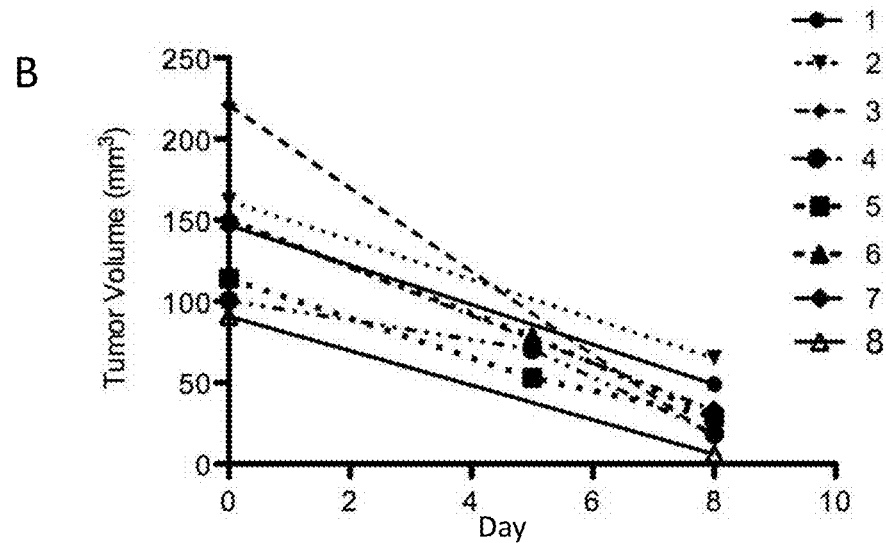

Control rats 1 and 2 received orthotopic implantation of C6 glioma, but were not treated with letrozole. For control rat 4, tumor volume was 146.5 mm³ 10 days after tumor cell implantation (Day 0) and increased to 179.4 mm³ and 192.2 mm³ on day 8. Similarly, for control rat 2 initial tumor volume was 119.5 mm³ and increased to 218.1 mm³ on day 5 and 378.4 mm³ on day 8. Similar increases in tumor volume were observed in all the rats in the control group, with average active tumor volume on day 0 and day 8/10 being 126.3±13.5 mm³ and 264.15 mm³, respectively (n=4). See FIG. 11(A).

In the treatment group, after the initial uPET/CT scan 10 days after tumor implantation, letrozole treatment was commenced. Rats received 4 mg/kg/day of letrozole via i.v. tail injection. Animals were scanned again 8-10 days post treatment to assess change in tumor volume. For treatment rat 8, tumor volume was 90.9 mm³ 10 days after tumor cell implantation (Day 0) and decreased to 5.8 mm³ day 8. Similarly, for treatment rat 4, initial tumor volume was 100.5 mm³ on Day 0 and decreased to 70.5 mm³ on Day 5 and 18.7 mm³ on Day 10. Similar regression in tumor volume was observed in all rats in the treatment group, with an average tumor volume on Day 0 of 150±48.5 mm³ and on Day 8/10 of 32.75±20 mm³ (n=8). The decrease in active tumor volume after letrozole treatment for 8-10 days was statistically significant (P=0.0001). See FIG. 11(B).

The rats of untreated control group were extremely sick by day 8 and showed neurological symptoms, porphyrin staining near eyes and nose, weight reduction, and loss of locomotor movements. Rats treated with letrozole showed no clinical symptoms and appeared healthy, with normal locomotion and normal body weights throughout the treatment period.

Example 7

In Vivo Anti-Tumor Efficacy Study of Oral Dosed Letrozole in Rats with Tumor Allografts Rats received tumor implantation as described in Example 6. 10 days after tumor implantation, letrozole administration began, via oral gavage at a dose of 4 mg/kg/day. Animals were scanned 5, 10, and 15 days after treatment period to observe change in tumor volume. After 15 days, treatment was stopped. Animals were scanned again on Day 45 (30 days post cessation of treatment). Regression of tumor size at Day 15 was similar to that of animals dosed via i.v. tail injection (Example 6). However, tumors recurred once treatment was stopped.

Example 8

Aromatase Expression in Rat Glioma Tissue

Figure 12:
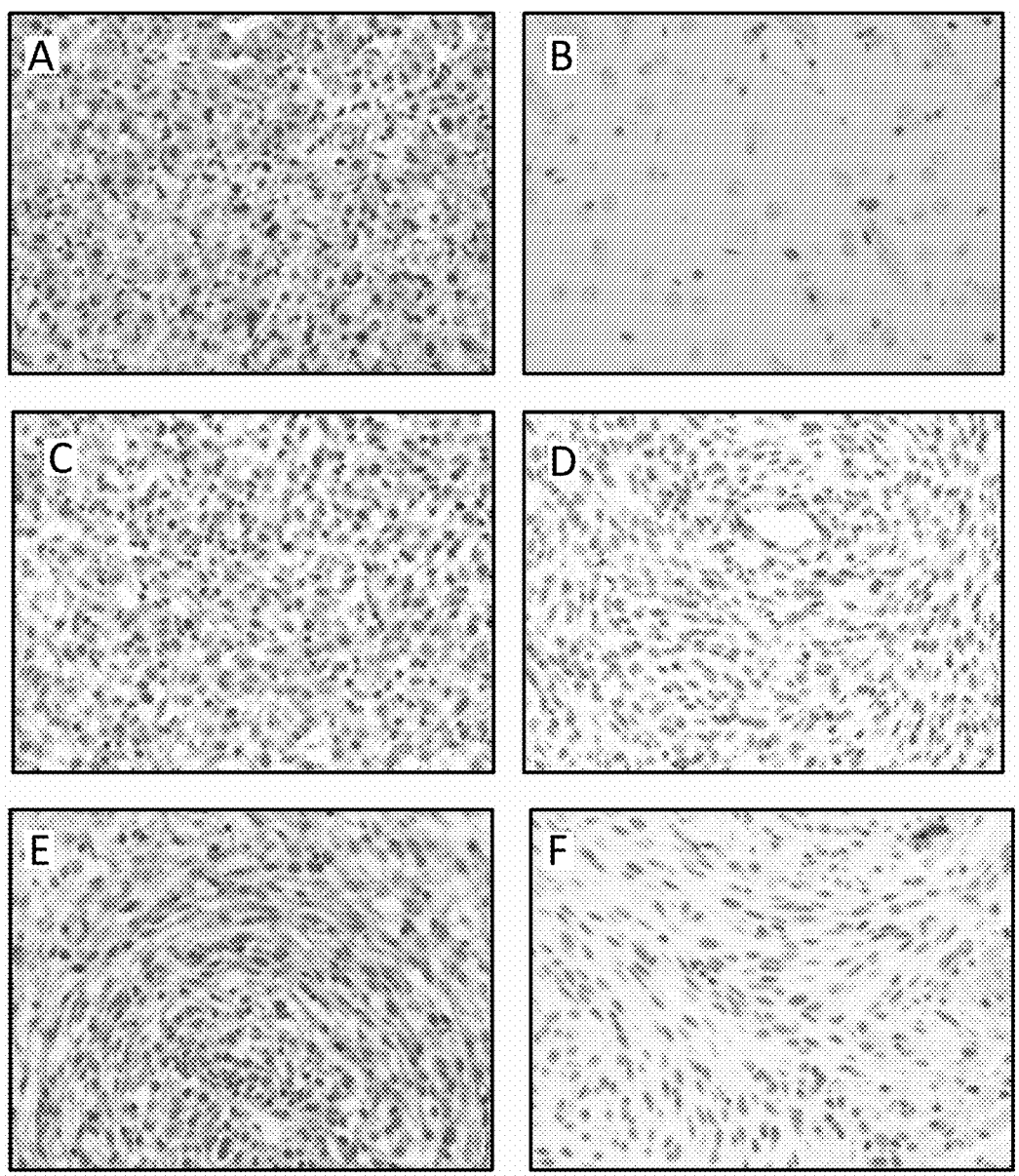
FIG. 12. Immunohistochemistry for aromatase expression in rat tissue sections. (A) rat ovary (positive control). (B) normal rat brain. (C-F) C6 glioma rat brains (Control group—(C), (E); Treatment group—(D), (F)).

Expression of aromatase in tumors from rats of both control and treatment groups was evaluated using immunohistochemical (IHC analysis). Rat ovary (FIG. 12(A)) was used as a positive control for aromatase expression. Normal brain region (FIG. 12 (B)) showed negligible aromatase expression. Brain tumor sections of rats of control group (FIG. 12 (C), (E)) showed high expression of aromatase, whereas tumor sections of treatment group (FIG. 12 (D), (F)) showed relatively low aromatase expression.

Example 9

Oral Versus Intravenous Administration of Letrozole in Rats

Brain pharmacokinetics of oral versus intravenous (i.v.) administration of letrozole were compared. Results are shown in Table 5 below:

TABLE 5

Comparison of Pharmacokinetic Data for Oral vs. I.V. Administration

| PK Parameter | 4 mg/kg i.v. injection (N = 9) | 4 mg/kg oral gavage (N = 4) |
|---|---|---|
| $T_{max}$ (hr) | 1.4 ± 0.6 | 5.75 ± 1.8 |
| $C_{max}$ (ng/ml) | 132 ± 79 | 176 ± 23 |
| $AUC_{0-8\ hr}$ (hr · ng/ml) | 583 ± 189 | 976 ± 162 |

As shown in Table 5, peak brain extracellular fluid (ECF) levels ($C_{max}$) reached after oral administration were similar to values obtained with i.v. injections (both dosed at 4 mg/kg). A slight delay in $T_{max}$ was observed, consistent with the delay of appearance of the drug in systemic circulation. $AUC_{0-8hr}$ after oral administration was found to be in a similar range to that of i.v. administration.

All documents cited are incorporated herein by reference; the citation of any document is not to be construed as an admission that it is prior art with respect to the present invention.

While particular embodiments of the present invention have been illustrated and described, it would be obvious to one skilled in the art that various other changes and modifications can be made without departing from the spirit and scope of the invention. It is therefore intended to cover in the appended claims all such changes and modifications that are within the scope of this invention.

What is claimed is:

1. A method of treating a primary brain tumor consisting of administering to a patient in need thereof a therapeutically effective amount of letrozole.

2. The method of claim 1, wherein the primary brain tumor is selected from the group consisting of glioma, meningeal tumor, medulloblastoma, and schwannoma.

3. The method of claim 2, wherein the primary brain tumor is a glioma selected from the group consisting of astrocytoma, oligodendroma, and ependymoma.

4. The method of claim 3, wherein the glioma is an astrocytoma selected from the group consisting of Grade I, Grade II, Grade III, and Grade IV.

5. The method of claim 2, wherein the primary brain tumor is a meningeal tumor selected from the group consisting of meningioma, atypical meningioma, anaplastic meningioma, hemangiopericytoma, anaplastic hemangiopericytoma, and hemangioblastoma.

6. The method of claim 1, wherein the therapeutically effective amount comprises a daily dose of from about 2.5 mg to about 60 mg.

7. The method of claim 1, wherein letrozole is administered orally, intravenously, or directly to the tumor.

8. The method of claim 7, wherein letrozole is administered orally.

9. The method of claim 1, wherein letrozole crosses the blood brain barrier.

10. The method of claim 1, wherein letrozole crosses the blood tumor barrier.

11. A method of treating a primary brain tumor consisting of administering to a patient in need thereof a combination consisting of a therapeutically effective amount of letrozole and one or more second active agent, wherein the one or more second active agent is selected from the group consisting of an anti-inflammatory agent, an immunosuppressive agent, a corticosteroid, and a chemotherapeutic agent selected from the group consisting of an alkylating agent, a platinum drug, an antimetabolite, an anti-tumor antibiotic, a topoisomerase inhibitor, a mitotic inhibitor, a differentiating agent, and a hormone therapy.

12. The method of claim 11, wherein the chemotherapeutic agent is selected from the group consisting of temozolamide, bevacizumab, and carmustine.

13. The method of claim 11, wherein the one or more second active agent is co-administered with letrozole.

14. A method of treating a primary brain tumor consisting of administering to a patient in need thereof a combination consisting of a therapeutically effective amount of letrozole and a tumor treating field (TTF) therapy.

15. A method of treating a primary brain tumor consisting of administering to a patient in need thereof a combination consisting of a therapeutically effective amount of letrozole and radiation therapy.

16. The method of claim 1, wherein administering comprises administering letrozole before, during, or after a surgery to remove the brain tumor.

17. A method of treating a primary brain tumor in a patient consisting of:
    (a) obtaining a biopsy of the primary brain tumor;
    (b) analyzing the biopsy to determine whether the primary brain tumor is a type of tumor that is responsive to letrozole treatment; and
    (c) administering a therapeutic amount of letrozole to the patient when the primary brain tumor is determined to be a type of tumor that is responsive to letrozole treatment.

18. A method of treating a primary brain tumor consisting of administering to a patient in need thereof a combination consisting of (1) a therapeutically effective amount of letrozole; and (2) a chemotherapeutic agent selected from the group consisting of temozolamide, bevacizumab, and carmustine.

* * * * *